United States Patent [19]

Singh et al.

[11] 4,374,771
[45] Feb. 22, 1983

[54] BLOCKED ISOCYANATE

[75] Inventors: Balwant Singh; Robert W. Novak, both of Stamford, Conn.

[73] Assignee: American Cyanamid Company, Stamford, Conn.

[21] Appl. No.: 355,821

[22] Filed: Mar. 8, 1982

[51] Int. Cl.³ .......................................... C07D 403/12
[52] U.S. Cl. ............................................. 260/239.3 R
[58] Field of Search ................................. 260/239.3 R

[56] References Cited

U.S. PATENT DOCUMENTS 3,304,291 2/1967 Dachs et al. ................. 260/239.3 R

OTHER PUBLICATIONS

Fukumoto et al., "Nippon Kagaku Zasshi", vol. 84, No. 9, pp. 736–740, (1963).
Duong et al., "Australian J. Chemistry", vol. 29, No. 12, pp. 2651–2665, (1976).

Primary Examiner—Robert T. Bond
Attorney, Agent, or Firm—Steven J. Hultquist

[57] ABSTRACT

The novel compound, N,N'-methylenebis (hexahydro-2-oxo-1H-azepine-1-carboxamide) which is useful as a blocked isocyanate to introduce the functionality of methylene diisocyanate and which is prepared by the reaction of isocyanic acid and caprolactam followed by reaction with formaldehyde.

3 Claims, No Drawings

BLOCKED ISOCYANATE

This invention relates to blocked isocyanates and in particular provides a novel carboxamide compound and process of its production.

Blocked isocyanates are frequently used, for example, in high solids coating formulations and also in powder coating formulations to improve the stability of the formulation on storage.

It is an important object of this invention to provide a new compound functioning as an e-caprolactam blocked methylene diisocyanate, N,N'-methylenebis (hexahydro-2-oxo-1H-azepine-1-carboxamide).

The blocked isocyanate of the invention is readily soluble in most solvents commonly used in liquid coating formulations and is also a solid at normal temperatures making it useful in preparation of powder coating formulations. In reaction with alcohols e-caprolactam is the leaving group. Calorimetric evidence suggests that the blocked isocyanate of the invention reacts with alcohols at lower temperatures than 4,4'-diphenyl methane diisocyanate (MDI) blocked with caprolactam and that the caprolactam polymerizes under cross-linking conditions to produce non-gaseous products which form uniform coatings essentially free from blistering. Coatings prepared with the blocking isocyanate of this invention are, moreover, characterized by light stability and absence of yellowing.

The blocked isocyanate of this invention in particularly desirable since it functions as if it were methylene diisocyanate in its reaction with alcohols. Methylene diisocyanate, being the lowest diisocyanate of the saturated hydrocarbon series, provides a high degree of cross-linking per unit weight.

The blocked isocyanate of this invention is prepared from hexahydro-2-oxo-1H-azepine-1-carboxamide by reaction with formaldehyde. The precursor carboxamide is a known compound which can be prepared in a two step process utilizing sodium hydride and ethylchlorformate (Austral. j. Chem 29 (12) 2651 (1976). In accordance with this invention, however, the precursor carboxamide is prepared from caprolactam by reaction with isocyanic acid.

EXAMPLE I

Hexahydro-2-Oxo-1H-Azepine-1-Carboxamide

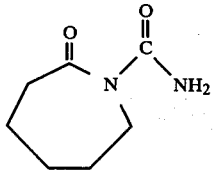
(I)

One mole of caprolactam dissolved in toluene is added to a solution of 1.25 moles of isocyanic acid (HNCO) in 20% toluene solution. 0.8 M mole of dibutyltin dilaurate is added to the resultant solution, and the mixture is then heated to 60° C. for a period of 17 hours. A 30% conversion to compound I is achieved. Toluene insoluble polymerization products of isocyanic acid are then filtered out, and the filtrate is stripped of solvent to about ½ of its volume. Additional charges of isocyanic acid in toluene solution are then added and the procedure repeated two or three times until the conversion of caprolactam to compound I is 95%+. Compound I can be isolated by crystallization.

EXAMPLE II

N,N'-methylenebis (hexahydro-2-oxo-1H-azepine-1-carboxamide)

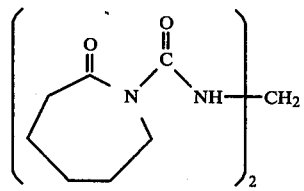
II

One mole of compound I dissolved in acetonitrile is added to 0.5 mole of 37% formaldehyde and 3.6 mmole of concentrated hydrochloric acid. The ensuing reaction continues at room temperature for at least four days after which compound II is recovered by adding the reaction mixture to ice-water and filtrating, recovering a crystalline product having a melting point of 114°–117° C.

EXAMPLE III

Hexahydro-2-Oxo-1H-Azepine-1-Carboxamide

One and a quarter moles of isocyanic acid (HNCO) in a 21% di-n-butyl ether solution is added to a suspension of one mole of caprolactam suspended in di-n-butyl ether at room temperature. The resultant mixture is then heated to 80° C. for a period of 4 hours with the appearance of a white solid. A 50% conversion to compound I is achieved. An additional 0.5 mole of isocyanic acid in di-n-butyl ether is added and the resulting solution heated at 80° C. for a period of 12 h. An 80% conversion to compound I is achieved. Compound I is isolated by cooling the solution to 0° C., filtering off the white precipitate and extracting compound I from this solid with methylene chloride and removing the solvent.

EXAMPLE IV

Hexahydro-2-Oxo-1H-Azepine-1-Carboxamide

One and one-tenth mole of isocyanic acid in a 21% glyme solution is added to a solution of 1.00 mole of caprolactam dissolved in glyme. The resultant mixture is then heated to 80° C. for a period od 20 h with the appearance of a white solid. An 85% conversion to compound I is achieved. Compound I can be isolated by standard purification technique.

EXAMPLE V

Coating Preparation

A 20% solution in cellosolve acetate of 13.5 parts by weight of compound II is mixed with 13.6 parts by weight of Acryloid AT 400 (a proprietary acrylic resin) to give an NCO/OH equivalancy of 1.1. Drawdowns are prepared on 4"×12" aluminum panels (Alodine 12005) using a 3.5 mil (wet) wirecator. After setting for ten minutes the panels are baked at 175° and 200° C. for 20 minutes. The panels cured at 175° with a film thickness of 1.0 mil show a knoop hardness of 4.6 and MEK resistance to mar of 10 and to remove of 200 rubs. The panels cured at 200° C., with a film thickness of 0.95 mil show a knoop hardness of 5.9 and MEK resistance of >200 to mar.

We claim:

1. N,N'-methylenebis (hexahydro-2-oxo-1H-azepine-1-carboxamide).

2. A process for the preparation of a blocked isocyanate which comprises reacting hexahydro-2-oxo-1H-azepine-1-carboxamide with formaldehyde to yield N,N'-methylenebis (hexahydro-2-oxo-1H-azepine-1-carboxamide).

3. A process for preparing hexahydro-2-oxo-1H-azepine-1-carboxamide which comprises reacting caprolactam with isocyanic acid.

* * * * *